United States Patent [19]

Kajfež et al.

[11] 3,996,222
[45] Dec. 7, 1976

[54] PIPERAZINE DERIVATIVES

[75] Inventors: Franjo Kajfež; Vesna Šunjić; Vitomir Šunjić, all of Chiasso, Switzerland

[73] Assignee: CRC Compagnia de Ricerca Chimica, Chiasso, Switzerland

[22] Filed: Apr. 10, 1974

[21] Appl. No.: 459,682

Related U.S. Application Data

[63] Continuation-in-part of Ser. No. 328,142, Jan. 30, 1973, abandoned.

[30] Foreign Application Priority Data

Feb. 1, 1972 Switzerland .................. 1420/72

[52] U.S. Cl. .................. 260/247.5 D; 424/248; 260/247.1 E
[51] Int. Cl.² .................. C07D 498/10
[58] Field of Search ............. 260/247.5 D

[56] References Cited

OTHER PUBLICATIONS

Light, J. Am. Pharmaceutical Assoc. vol. XLVI No. 5, 1957, pp. 279–287 (Sci ed.).
Baltzly, J.A.C.S. vol. 66, 1944, pp. 263–266.
Baltzly, J.A.C.S. vol. 77, 1955, pp. 4809–4811.

*Primary Examiner*—Henry R. Jiles
*Assistant Examiner*—R. W. Ramsuer
*Attorney, Agent, or Firm*—Haseltine, Lake & Waters

[57] ABSTRACT

A process for the production of piperazine derivatives including the formation of compounds having the general formula

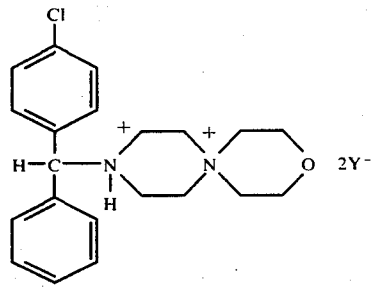

wherein Y is a halogen atom, $SO_3H^-$, $SO_4^{--}$ or another anion. The compounds exhibit cytostatic, cancer retardant and tranquilizing properties.

1 Claim, No Drawings

PIPERAZINE DERIVATIVES

This application is a continuation-in-part of Ser. No. 328,142, filed Jan. 30, 1973, now abandoned.

FIELD OF THE INVENTION

The present invention relates to a process for the production of piperazine derivatives.

In essence, the process of the present invention relates to the formulation or manufacture of compounds having the general formula

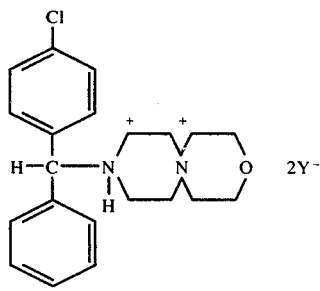

wherein Y is a halogen atom, $SO_3^-$, $SO_4^{--}$ or another anion.

SUMMARY OF THE INVENTION

Compounds having the Formula I may be obtained from a compound having the formula

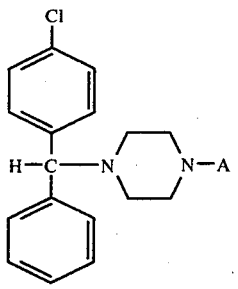

Wherein A is hydrogen atom by reacting with a compound having the formula $$X-CH_2-CH_2-O-CH_2-CH_2-X \qquad III.$$

in which X is a halogen atom.

Compounds of formula I can also be obtained from compounds of formula II when A = $-CH_2CH_2-O-CH_2CH_2-OH$ namely by halogenation of the hydroxyl group with a halogenating agent, preferably with thionyl chloride or phosphorus tribromide.

Upon halogenation there is first obtained a compound of formula II wherein A is $-CH_2CH_2-O-CH_2CH_2-$ Hal in the form of the hydrohalide. By neutralization of the hydrohalide, the free base is obtained which then cyclizes to compounds of formula I. The cyclization takes place in an inert organic solvent and in the presence of anhydrous acids (preferably hydrogen chloride saturated ethanol or in anhydrous formic acid). Salts with inorganic or organic acids from the compounds of Formula I are obtained by a simple dissolving of a pure base (which is generally present as an oil) of the compound having the Formula I in an inert organic solvent medium (preferably ethanol) which has been previously saturated with acid (by introduction of gaseous HCl, HBr or any equivalent amount of anhydrous organic acid.

Also salts can be obtained by simple exchange of anion Y by another anion. This exchange is carried out in an inert organic solvent or in water in the presence of a salt of the other anion.

For example compounds having the Formula I in which Y = I, may be obtained from compounds having the Formula I in which Y = Cl or Br, by the so-called Finkelstein reaction in which there is effected a substitution of the chlorine or bromine by iodine through the intermediary of potassium iodide in an inert organic solvent medium.

Compounds of Formula I, and their salts, are new and heretofore undisclosed compounds which exhibit good cytostatic, cancer retardant and tranquilizing properties.

Furthermore, their toxicities are extremely low in comparison with previously known cytostatic and cancer retardant pharmaceuticals. The toxicity per os has the following values for:

| | | |
|---|---|---|
| X = Cl | $LD_{50}$ = 315.5 | mg/kg |
| X = Br | $LD_{50}$ = 308.5 | '' |
| X = I | $LD_{50}$ = 276.7 | '' |

Intraperitonials utilized in dosages of 1–2 mg/kg evinced very good inhibiting effects for Hepatone AH 130 of the Walker carcinoma, for the Erlich carcinoma, for the Sarkome 180 and for the Oberling-Guerin-Guerin (OGG) Mieloma, which were artificially produced in mice.

Furthermore, in parallel conducted experiments, the compounds having the general Formula I effected an increase in the life span of animals having tumors. These experiments were carried out on albino mice having weights of 120 to 240 grams.

Additionally, no histological changes in the intestinal epithelium were observed, as well as no changes in the Testi.

Compounds having the general Formula I were injected in the animals intra-peritoneally five days after the transplanting of the tumors.

In Yoshido AH 130 Hepatome and Walker carcinoma, the tumor disappeared completely upon direct contact between the substances and the tumorous cells.

PREFERRED EXAMPLES OF THE INVENTION

In order to provide a better understanding of the present invention, the following examples are herewith given, which in no manner limit the scope of present invention and are to be considered as being merely for illustrative purposes.

EXAMPLE 1

80 grams of a 40% solution of 1-(p-chlorobenzhydryl)-4-piperazine in m-xylene (32 g $C_{17}H_{19}ClN_2$-Molecular Weight 282.780 or 0.113 Mol) and 355 ml. 2,2'-dichloro-diethylether (440 g = 3.08 Mol $C_4H_8Cl_2O$-Molecular Weight = 143.022, 27-fold excess) were mixed in a flask and heated under reflux. After 13 hours the $N^1$-(4'-chlorobenzhydryl)-$N^4$-spiromorpholino-piperazinium chloride-hydrochloride precipitate was filtered by suction, and then washed with ether.

Recrystallization was effected from an aqueous ethanol and ether mixture. Obtained was 35.2 grams (72%) N$^1$-(4'-chlorobenzhydryl)-N$^4$-chlorobenzhydryl)-N$^4$-spiromorpholinopiperazinium chloride hydrochloride having a melting point of 282° to 285° C.

| Analysis: | C$_{21}$H$_{27}$Cl$_3$N$_2$O | Molecular Weight: 429.834 |
|---|---|---|
| Calculated: | C 58.68 | H 6.33 | N 6.52% |
| Obtained: | C 58.42 | H 6.36 | N 6.40% |
| Melting Point: | 286–288° C | | |

I.R. Spectrum (KBr) 2940 (—CH$_2$—), 2440 (≡NH+), 1600 (Phenyl), 1450 (—CH$_2$—), 1250 (C—O—C) cm$^{-1}$.

EXAMPLE 2

The process was carried out similarly to that of Example 1, however, in lieu of 2,2'-dichloro-diethylether there was utilized 2,2'-dibromodiethylether, thereby resulting in a 90% yield of N$^1$-(4-chlorobenzhydryl)-N$^4$-spiro-morpholinopiperazinium bromide hydrobromide having a melting point of 268°–270° C. (from ethanol-ether).

| Analysis: | C$_{21}$H$_{27}$Br$_2$ClN$_2$O | Molecular Weight: 518.731 |
|---|---|---|
| Calculated: | C 48.63 | H 5.24 | N 5.40% |
| Obtained: | C 48.75 | H 5.46 | N 5.25% |

EXAMPLE 3

A process was carried out as described in Example 1, however, the crystals which were precipitated after heating were dissolved in a 10% NaOH solution and the aqueous layer extracted by means of chloroform. The chloroform extract was dried, the chloroform distilled off, and the residual oil added to 600 ml. of ethanol saturated with hydrogen chloride. After a period of time, there were precipitated crystals of N$^1$-(4'-chlorobenzhydryl)-N$^4$-spiromorpholino-piperazinium-chloride hydrochloride. The yield of product was 70% having a melting point of 285-286° C.

EXAMPLE 4:

2.58 grans N$^1$-(4'-chlorobenzhydryl)-N$^4$-spiromopholino-piperazinium chloride hydrochloride (C$_{21}$H$_{27}$Cl$_3$N$_2$O, Molecular Weight 429.834, in effect, 6 millimoles) were dissolved in distilled water and neutralized with K$_2$CO$_3$. The water was completely evaporated, 150 ml. of acetone and 1.9 gKI (Mol. Wt. 166.02 = 12 millimoles) were added and stirred under reflux for 5.5 hours. The formed precipitate (2.9 grms.) was filtered by suction and the acetone filtrate reduced to a smaller volume. The separated precipitate was then again filtered by suction (1.5grms.). The combined precipitates were then stirred in cold water in order to dissolve the resultant KCl and excess of KI. The remainder was filtered, dried and 2.9 grams (100%) N$^1$-(4'-chlorobenzhydryl)-N$^4$-spiromor-pholinopiperazinium iodide was obtained, having a melting point of 276° to 278° C. Recrystallization from hot ethanol resulted in a melting point of 289° to 280.5° C.

| Analysis: | C$_{21}$H$_{28}$IN$_2$O | Molecular Weight: 484.801 |
|---|---|---|
| Calculated: | C 52.03 | H 5.41 | N 5.78% |
| Obtained: | C 52.32 | H 5.62 | N 5.52% |

I.R. Spectrum (KBr) 2980 (CH—), 1600 (Phenyl), 1485 (—CH$_2$—), 1120 and 1085 (C—O—C) cm$^{-1}$.

EXAMPLE 5:

3.0 grams of N$^1$-(4'-chlorobenzhydryl)-N$^4$ [2-(2-hydroxyethoxyethyl] piperazinium-hydrochloride (C$_{21}$H$_{28}$Cl$_2$N$_2$O$_2$, Molecular Wt. 411.385, 7.3 millimoles) were dissolved in a flask in 30 ml. of warm nitromethane (CH$_3$NO$_2$, Boiling Point 99°–101° C., d$_4^{20}$ = 1.134). During cooling in an ice bath, there is added drop-wise, a mixture of CH$_3$NO$_2$(7.5 ml.) and phosphorus tribromide (PBr$_3$ 2.5 milliliters d$_4^{18}$ — 2.852, Molecular Weight 270.72, 7.1 grams = 26.3 millimole, 12-fold excess). After stirring for 24 hours at room temperature, the excess of phosphorus tribromide was destroyed with water. The mixture was then neutralized with NaHCO$_3$ and sodium-acetate. The nitromethane and aqueous layer was then separated. The aqueous layer was then further extracted two times with nitromethane. The nitromethane extracts were then combined and dried with sodium sulphate (calcined). The nitromethane was then distilled off. The residue was a yellow product (2.3 grams, 72%), Melting Point 244-247° C. Through recrystallization from ethanol-ether (1:2) there was obtained 1.46 grams N$^1$-(4'-chlorobenzhydryl) -N$^4$-spiromorpholinopiperazinium bromide. Melting Point 248°–251° C.

| Analysis: | C$_{21}$H$_{26}$BrClN$_2$O | Molecular Weight: 437.813 |
|---|---|---|
| Calculated: | C 57.62 | H 5.98 | N 6.40% |
| Obtained: | C 57.74 | H 6.02 | N 6.38% |

While there has been shown what is considered to be the preferred embodiment of the invention, it will be obvious that modifications may be made which come within the scope of the disclosure of the specification.

Suitable inert organic solvents for use in preparing the compounds of the invention include nitromethane, acetonitrile, nitrobenzene, chloroform, acetone, dioxane, dimethyl sulfoxide, toluene, xylene and benzene.

We claim:
1. A compound having the formula

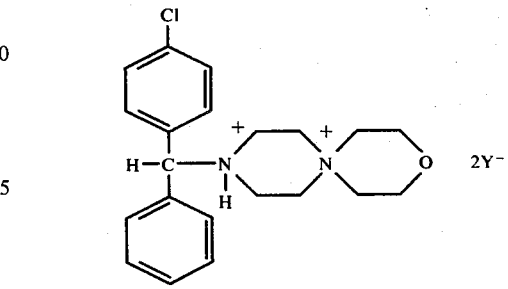

wherein Y is a halogen.

* * * * *